(12) United States Patent
Filho

(10) Patent No.: US 6,666,685 B2
(45) Date of Patent: Dec. 23, 2003

(54) DISPOSITION INTRODUCED IN AN ASSEMBLY OF ELEMENTS USED IN OSTEO-INTEGRATED IMPLANTS

(76) Inventor: Plauto Pires De Almeida Filho, Rua Emboacava, 689, Parque da Moóca, São Paulo (BR)

( * ) Notice: Subject to any disclaimer, the term of this patent is extended or adjusted under 35 U.S.C. 154(b) by 0 days.

(21) Appl. No.: 10/050,918

(22) Filed: Jan. 22, 2002

(65) Prior Publication Data

US 2002/0115040 A1 Aug. 22, 2002

(30) Foreign Application Priority Data

Feb. 19, 2001 (BR) ............................ 8100305 U

(51) Int. Cl.$^7$ ................................................ A61C 8/00
(52) U.S. Cl. ...................... 433/173; 433/172; 623/16.11
(58) Field of Search .................. 433/172, 173, 433/174, 175, 176, 201.1; 623/16.11, 17.17, 18.11; 606/72, 73

(56) References Cited

U.S. PATENT DOCUMENTS

| | | | | |
|---|---|---|---|---|
| 5,125,840 A | * | 6/1992 | Durr et al. .................. | 433/173 |
| 5,282,746 A | * | 2/1994 | Sellers et al. ............... | 433/172 |
| 5,292,252 A | * | 3/1994 | Nickerson et al. .......... | 433/173 |
| 5,368,483 A | * | 11/1994 | Sutter et al. ................ | 433/173 |
| 5,533,898 A | * | 7/1996 | Mena .......................... | 433/173 |
| 5,622,500 A | * | 4/1997 | Niznick ...................... | 433/173 |
| 5,759,034 A | * | 6/1998 | Daftary ...................... | 433/173 |
| 5,816,809 A | * | 10/1998 | Sapkos ........................ | 433/172 |
| 6,032,677 A | * | 3/2000 | Blechman et al. .......... | 433/173 |
| 6,126,662 A | * | 10/2000 | Carmichael et al. ........ | 433/173 |
| 6,257,890 B1 | * | 7/2001 | Khoury et al. .............. | 433/173 |
| 6,283,752 B1 | * | 9/2001 | Kumar ....................... | 433/172 |

OTHER PUBLICATIONS

One–page advertisement in Brazil by Sulbri relating to a symposium on dental implants entitled "I Simposio sul–brasileiro de Implantodontia," showing prior art dental implant devices that pre–date Feb. 19, 2001.

One–page advertisement in Brazil by Emfils relating to dental implants (date of ad unknown but devices shown pre–date Feb. 19, 2001).

One–page advertisement in Brazil relating to hexagon dental implants entitled "Implants—Plataforma Regular, Implantes com Rosca e Hexagono" (date of advertisement unknown—but devices shown predate Feb. 19, 2001).

One–page advertisement in Brazil by Intra–Lock System relating to dental implants (date of ad unknown but devices shown pre–date Feb. 19, 2001).

One–page advertisement in Brazil by De Bortoli relating to dental implants (date of ad unknown but devices shown pre–date Feb. 19, 2001).

\* cited by examiner

*Primary Examiner*—John J. Wilson
(74) *Attorney, Agent, or Firm*—Dickinson Wright PLLC

(57) ABSTRACT

The present invention refers to a disposition introduced in an assembly of elements used in osteo-integrated implants, basically defined by a prosthesis support, a reception element of said prosthesis support, said reception element being introduced in the jaws of the patient and placing element that promotes the introduction of the reception element (11) into the jaws of the patient.

19 Claims, 3 Drawing Sheets

US 6,666,685 B2

DISPOSITION INTRODUCED IN AN ASSEMBLY OF ELEMENTS USED IN OSTEO-INTEGRATED IMPLANTS

RELATED APPLICATION

The present application claims priority from a Brazilian National Patent Application, Serial No. MU 8100305, filed on Feb. 19, 2001.

BACKGROUND OF THE INVENTION

The present invention relates to a disposition introduced in an assembly of elements used in osteo-integrated implants which assembly enables the performance of an implant in a practical, efficient and safe manner, considering the surgery and the prosthesis.

Currently, the known elements for osteo-integrated implants are defined by a prosthesis support, a reception element of this prosthesis support introduced by interference or threading into the jaws of the patient through a placing element, the placing element, according to most of the manufacturers, being comprised basically of a cylindrical tubular body, externally threaded in its whole extension and provided with a blind threaded surface inner hole, presenting on its lower extremity a hole for the osteo-integration and on the upper part a short height hexagonal nut, that receives the tool to place the thread in the jaw. Aided by a placing tool, the reception element is introduced in the jaw, the hexagonal nut being directed upwards.

Despite being widely used by those skilled in the art, it was noticed that known elements and systems present some mechanical design drawbacks that create problems in the course of time, the most frequent being the loosening and more rarely the thread breakage and loss of the initial strength of the linking screw between the prosthesis fixation and the reception element (with a gap between the parts, the introduction and proliferation of bacteria in the implant may be considered). Should this occur, the patient has to return to the professional to check and tighten the parts (when the screw is broken, the problem is worsened, sometimes with the total loss of the implant).

SUMMARY OF THE INVENTION

One of the objectives of the present invention is to provide an assembly of elements used in osteo-integrated implants that aims, among other objectives, at easing the assembly of the implant, reducing the time spent to manufacture it, saving tools and time with the stoppage of machinery to change tools, and briefly, causing the product to become cheaper, favoring the manufacturer and the final user.

Another objective of the present invention is to provide an assembly of elements used in osteo-integrated implants that is mainly able to reduce the problems of loosening or element breakage, introduction and proliferation of bacteria, allowing the professional to offer a higher assurance in results and markedly reducing the return of dissatisfied patients, i.e., the patient will only return for a periodic inspection, at the discretion of the professional.

These and other objectives are attained through an assembly of elements used in osteo-integrated implants, which, according to the present invention, is comprised of a prosthesis support and a reception element of the latter, provided with a building system that allows for a substantially perfect fit among them (conical interference), being virtually impossible to create a non-union among them.

The components related to the implant include the following: implant cap; healers; molding pins and bearing for the prosthesis over implant, and adopt the same conical interference system and closure with a screw with hemispherical resolution.

Currently, prosthetic components with screw and thread are used, but due to the loads and chewing forces, with the course of time there is the possibility of breaking the screw of the prosthetic component or, more frequently, the loosening and maybe the loss of the prosthetic component.

Thus, it is an objective of the present invention to provide a disposition introduced in an assembly of elements used in osteo-integrated implants that aims basically at removing first the drawbacks mentioned above and further providing a number of other advantages, such as:

to remove air, saliva and blood from the inner part of the implant; there is no loss of the prosthetic component (abutment); there is no bacterial proliferation; it may be used for single and multiple prosthesis; simplified molding; simplified prosthesis building; higher retention of the clinical crown in the prosthetic component; it may be used either for cemented prosthesis or for screwed prosthesis; there is no possibility of prosthetic component screw breakage; the holes of the abutment, in addition to acting for the placement of the part in buccal places that are not so opened, aim at the retention of the clinical crown, the distribution of the chewing loads will be absorbed by the conical area, applied only at the sides of the implant, not affecting the compensation area.

BRIEF DESCRIPTION OF THE DRAWINGS

In order to better understand the innovation now proposed, it will be described as follows, regarding the attached drawings, in which.

DETAILED DESCRIPTION OF THE INVENTION

Figure 1:
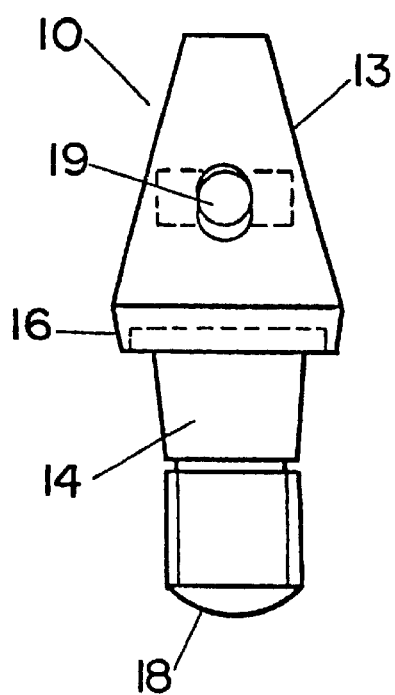
FIG. 1 is an elevation view of the prosthesis support.
Figure 2:
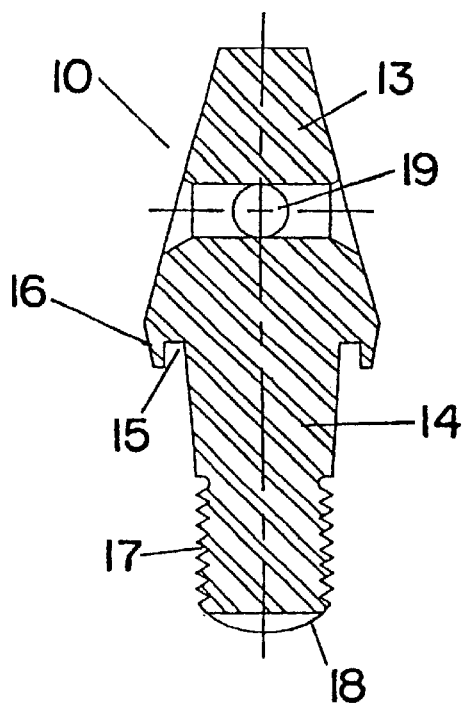
FIG. 2 is a diametric section view of the prosthesis support.
Figure 3:
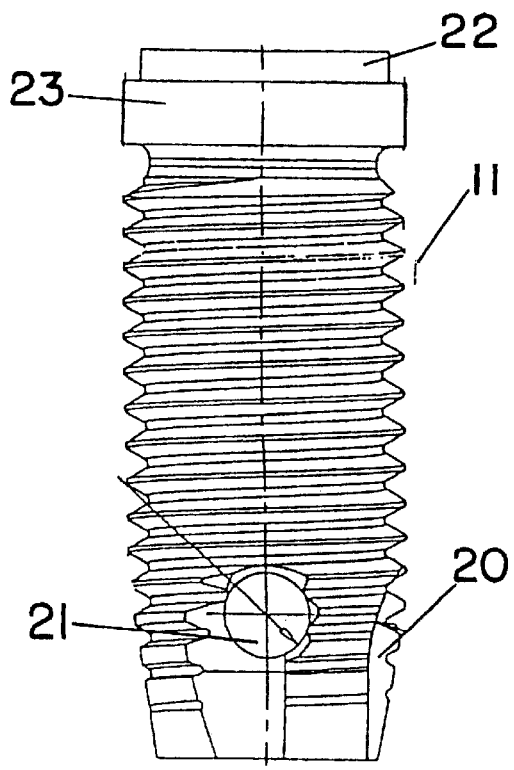
FIG. 3 is an elevation view of the reception element of the prosthesis support.
Figure 4:
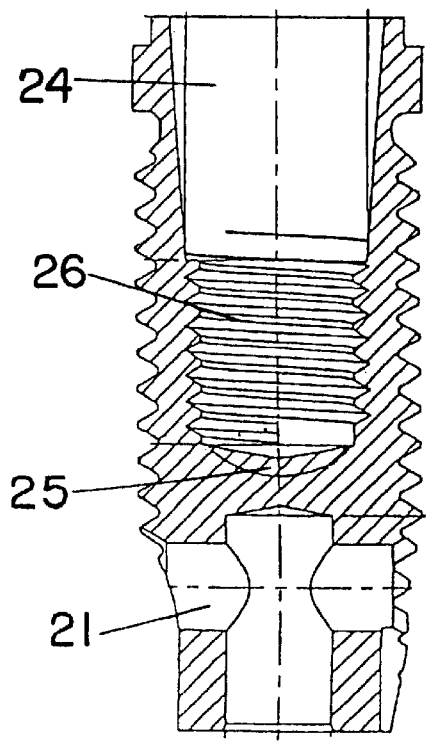
FIG. 4 is a section view of the reception element of the prosthesis support.
Figure 5:
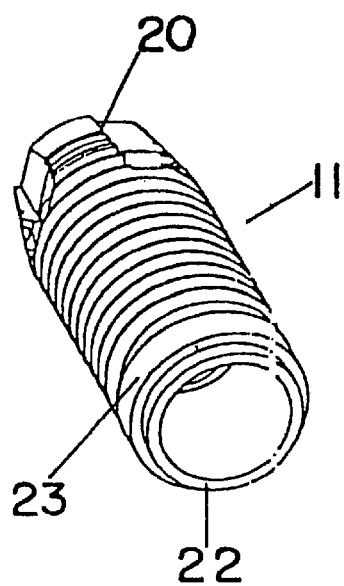
FIG. 5 are perspective views of the reception element of the prosthesis support.
Figure 5:
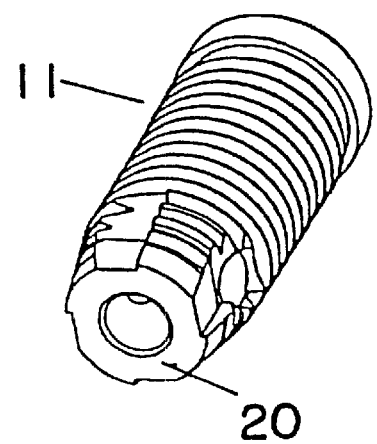
Figure 6:
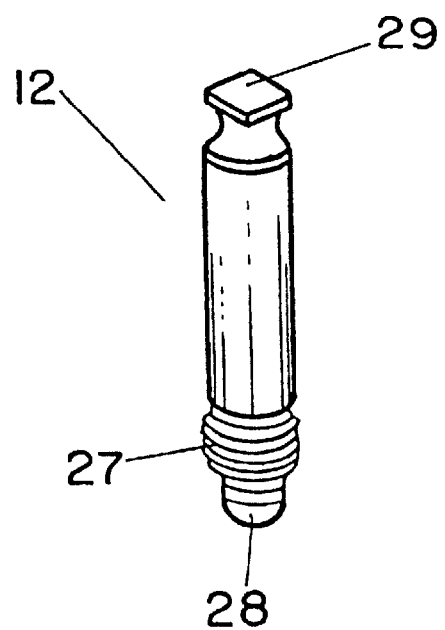
FIG. 6 is a perspective view of the placing element.
Figure 7:
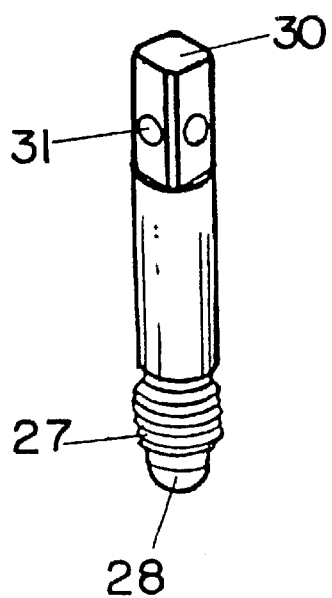
FIG. 7 is a perspective view of a building variant of the placing element.

According to the figures mentioned above, the assembly of elements used in osteo-integrated implants are basically defined by a prosthesis support (10), a reception element (11) of said prosthesis support, said reception element being introduced in the patient's jaw; and a placing element (12) that performs the introduction of the reception element (11) into the patient's jaw. The prosthesis support (10) comprises a first trunk-conical upper part (13) above a second trunk-conical part (14) with a smaller diameter than the first part, and between a circular and peripheral channel is defined (15) surrounded by a peripheral sleeve (16) projected from the first trunk-conical part (13) and that preferably presents a surface slightly sloped downwards and inwards. Approximately 50% of the lower half of the side of the second trunk-conical part (14) is preferably provided with an external thread (17), the lower extremity of this second part being defined by a rounded or hemispherical surface (18). The first trunk-conical part (13) is provided with a passage side hole (19).

The reception element (11) of this prosthesis support (10), and that should be introduced into the jaw of the patient, is comprised of a substantially completely externally threaded cylindrical part, its lower extremity being a male self-tapping part (20) in order to make or correct the thread and a hole (21) for the osteo-integration, and at the upper part of this cylindrical part, two rectified rings are provided, with different diameters, an upper one with a smaller diameter and preferably being shorter (22) and a lower one with a larger diameter and preferably being taller (23), both being integrated in the cylindrical part itself and act as sealing elements when the prosthesis support (10) and the reception element (11) are connected. The reception element (11) is internally provided with a rectified conical part (24) closed by a rounded or hemispherical base (25) and presenting its lower third of its total height with a threaded surface (26).

The placing element (12) that promotes the introduction of the reception element (11) into the jaws of the patient is preferably defined by a cylindrical body presenting at its lower part a threaded part (27) followed by a rounded or hemispherical base (28), the upper extremity of this placing incorporating a projection of the square base (29) in order to introduce the manual tool or the engine. Optionally, this upper extremity of the placing element (12) is defined by an extreme part of a substantially square section (30) with rounded vertices, provided with four side holes (31).

Assembled in the manner mentioned above, the assembly of elements used in osteo-integrated implants are used as follows: the reception element (11) of the prosthesis support (10) is introduced into the patient's jaw through the placing element (12), being that to do so, this latter element is introduced into the rectified conical part (24) of the reception element (11) so as to thread its threaded part (27) into the threaded surface (26) of the reception element (11), so that the hemispherical base (28) of the placing element (12) is housed in the inner surface of the hemispherical base (25) of the reception element (11). The placing element (12) is threaded into the reception element (11) until it finds resistance, this occurring, the reception element (11) is preferably locked with a tweezer or pliers. After this lock, the placing element (12) is removed from the reception element (11) unthreading the parts.

Once placed, the reception element (11) receives the prosthesis support (10) so that the external thread (17) of the second trunk-conical part (14) is threaded into the threaded surface (26) of the reception element (11), placing the hemispherical surface (18) of the second trunk-conical part (14) housed in the inner surface of the hemispherical base (25) of the reception element (11). In this fixation, the circular and peripheral channel (15) surrounded by the peripheral sleeve (16) projected from the first trunk-conical part (13) of the prosthesis support (10) is perfectly fitted in the peripheral rim of the upper ring with a smaller diameter and shorter (22) of the reception element (11), so that the peripheral sleeve (16) surrounds the side of the lower ring with larger diameter and taller (23) of this reception element (11).

Said fixation described above between the prosthesis support and the reception element allows, through the existence and the interactive placement of the hemispherical bases mentioned above, that either the air existing in the insert or reception element (11) or any liquid or blood residue be removed, avoiding bacterial proliferation and, consequently unpleasant odors. Moreover, the perfect junction of the circular and peripheral channel (15) of the prosthesis support (10) with the peripheral upper ring rim, with a smaller diameter and shorter height (22) of the reception element (11), placing the peripheral sleeve (16) around the side of the lower ring with a larger diameter and taller height (23) of this reception element (11), providing a total stability to the assembly, forming a tight seal between the parts, in addition to that also provided by the junction of the rectified conical part (24) of the reception element (11) and the second trunk-conical part (14) of the prosthesis support (10). The frame and the placement of the peripheral sleeve (16) described above further allows a faster gum integration, and it should be noted that regarding the prosthesis support (10), the frame of the first trunk-conical part (13) provided with a passage side hole (19) may assume various embodiments, depending on the need of the cosmetic part. Regarding the holes (19), they should be always present, since in addition to acting in the placement of the part and final strength application, they also act in the retention of the clinical crown or resin in the final application of the cosmetic part.

Figure 8:
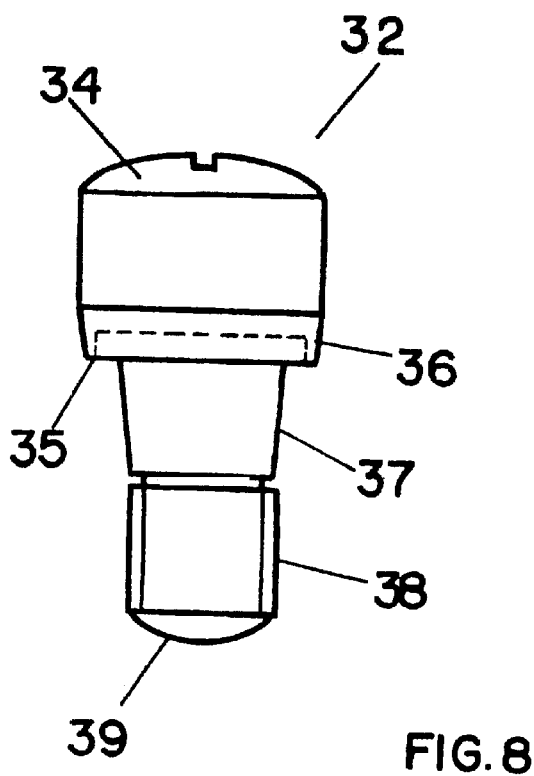
FIG. 8 is an elevation view of a healing element.
Figure 9:
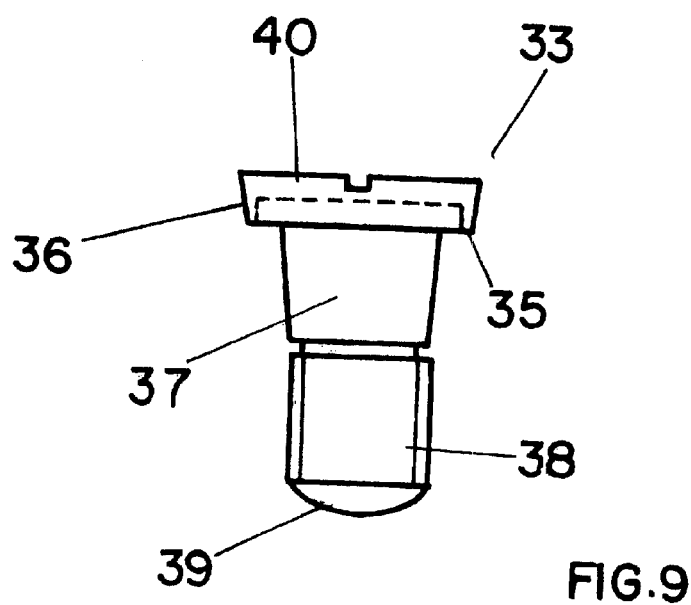
FIG. 9 is an elevation view of an implant cap.

As illustrated in FIGS. 8 and 9 of the drawing, a healing element (32) and an implant cap (33) are adapted to the reception element (11) in different steps and clinical procedures before the adaptation of said prosthesis support (10). To do so, the healing element (32) comprises the approximate shape of a cylindrical head screw (34) with a slightly domed surface centrally provided with a diametric crack, said cylindrical head being provided in its lower part with a circular and peripheral channel (35) surrounded by a peripheral sleeve (36), and from said sleeve a truck-conical part (37) is projected, presenting approximately its lower half provided with an external thread (38) which lower extremity being defined by a rounded or hemispherical surface (39). The implant cap (33) also comprises the approximate shape of a cylindrical head screw and flat surface (40) and presents in its lower part the same characteristics of the healing element (32), i.e., the circular and peripheral channel (35); the peripheral sleeve (36); the trunk-conical part (37) presenting approximately its lower half provided with an external thread (38) which lower extremity is defined by a hemispherical surface (39).

Thus, with this new dental prosthesis implant system, the load transfer will be always equal and at the conical interference, the higher the loads, higher the locking and annulment of the radial loads, assuring safety for the professional and for the patient. In an eventual need to remove the prosthesis, the system is easy and safe, not allowing the loss of the bone implant already carried out. The risk of loosening being reduced to zero, the return of the patient to the office will only occur in order to carry out periodical checks at the discretion of the professional.

What is claimed is:

1. An assembly used in osteo-integrated implants, comprising:

a prosthesis support having a first trunk-conical part above a second trunk-conical part, wherein said second trunk-conical part is smaller in diameter than said first trunk-conical part, wherein in between said first and second trunk-conical parts a circular channel is defined by a peripheral sleeve projected from said first trunk-conical part, wherein the lower portion of said second trunk-conical part has a threaded exterior followed by a lower extremity substantially defined by a rounded surface;

a reception element comprising an externally threaded cylindrical part having a male self-tapping part on the lower extremity thereof, wherein the upper part of said cylindrical part has first and second rings, wherein said first ring has a smaller diameter than said second ring, and said first and second rings are adapted such that they substantially mate with said circular channel and peripheral sleeve of said prosthesis support; and wherein said reception element is internally provided with a conical surface that substantially mates with said second trunk-conical part of said prosthesis support, an internal threaded section that substantially mates with said threaded exterior of said second trunk-conical part, and a rounded base that substantially mates with said rounded surface of said second trunk-conical part of said prosthesis support.

2. The assembly of claim 1, wherein the exterior surface of said peripheral sleeve is slightly sloped downwards and inwards from said first trunk-conical part.

3. The assembly of claim 1, wherein about one-half of said lower portion of said second trunk-conical part is provided with said threaded exterior.

4. The assembly of claim 1, wherein said first trunk-conical part is provided with a passage side hole.

5. The assembly of claim 1, wherein said cylindrical part of said reception element has a hole for osteo-integration.

6. The assembly of claim 1, wherein said first ring is shorter than said second ring.

7. The assembly of claim 6, wherein said first and second rings are integrated with said cylindrical part.

8. The assembly of claim 1, wherein said first ring has a substantially vertical exterior wall, and said circular channel has a substantially vertical interior wall, wherein said exterior and interior walls are adapted such that they form a substantial interference fit, such that no space is formed through which bacteria and impurities can enter into said reception element.

9. The assembly of claim 1, wherein a placing element for promoting the introduction of the reception element into a jaw of a patient is provided.

10. The assembly of claim 9, wherein said placing element is defined by a body having a threaded lower portion followed by a rounded base, wherein an upper portion of said placing element has a projection comprising a square base.

11. The assembly of claim 9, wherein said placing element is defined by a body having a threaded lower portion followed by a rounded base, wherein an upper portion of said placing element is defined by an extreme part with a substantially square section having rounded vertices and four side holes.

12. The assembly of claim 1, wherein a healing element is provided that can be fitted into said reception element.

13. The assembly of claim 12, wherein said healing element comprises a head screw and first and second trunk portions, wherein between said first and second trunk portions a circular channel is defined by a peripheral sleeve projected from said first trunk portion, wherein said circular channel and peripheral sleeve of said healing element are adapted such that they form a substantial interference fit with said first and second rings of said reception element.

14. The assembly of claim 13, wherein said second trunk portion has a conical portion that substantially mates with said conical surface of said reception element, an external threaded portion that substantially mates with said internal threaded section of said reception element, and a lower rounded surface that substantially mates with said rounded base of said reception element.

15. The assembly of claim 13, wherein said head screw has a slightly domed surface centrally provided with a diametric crack.

16. The assembly of claim 1, wherein an implant cap is provided that can be fitted into said reception element.

17. The assembly of claim 16, wherein said implant cap comprises a head screw having extended on a lower part thereof a circular channel defined by a peripheral sleeve, wherein said circular channel and peripheral sleeve of said implant cap are adapted such that they form a substantial interference fit with said first and second rings of said reception element.

18. The assembly of claim 17, wherein a trunk portion is extended below said head screw, said trunk portion having a conical portion that substantially mates with said conical surface of said reception element, an external threaded portion that substantially mates with said internal threaded section of said reception element, and a lower rounded surface that substantially mates with said rounded base of said reception element.

19. An assembly used in osteo-integrated implants, comprising:

a prosthesis support having a first trunk part above a second trunk part, wherein said trunk part is smaller in diameter than said first trunk part, wherein in between said first and second trunk parts a circular channel is defined by a peripheral sleeve projected from said first trunk part; and a reception element comprising an externally threaded cylindrical part, wherein the upper part of said cylindrical part has first and second rings, wherein said first ring has a smaller diameter than said second ring, and said first and second rings are adapted such that they form a substantial interference fit with said circular channel and peripheral sleeve of said prosthesis support, said reception element being internally provided with a conical surface that substantially mates with a conical surface of said second trunk part of said prosthesis support, an internal threaded section that substantially mates with a threaded exterior of said second trunk part, and a rounded base that substantially mates with a rounded surface located on a lower extremity of said prosthesis support.

* * * * *